(12) United States Patent
Salameh et al.

(10) Patent No.: US 10,691,574 B2
(45) Date of Patent: *Jun. 23, 2020

(54) COMPATIBILITY CHECK FOR CONTINUOUS GLUCOSE MONITORING APPLICATION

(71) Applicant: DexCom, Inc., San Diego, CA (US)

(72) Inventors: Issa Sami Salameh, San Diego, CA (US); Douglas William Burnette, San Diego, CA (US); Tifo Vu Hoang, San Marcos, CA (US); Steven David King, San Diego, CA (US); Stephen M. Madigan, San Diego, CA (US); Michael Robert Mensinger, San Diego, CA (US); Andrew Attila Pal, San Diego, CA (US); Michael Ranen Tyler, Carlsbad, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/334,160

(22) Filed: Oct. 25, 2016

(65) Prior Publication Data

US 2017/0132120 A1    May 11, 2017

Related U.S. Application Data

(63) Continuation of application No. 15/333,552, filed on Oct. 25, 2016, now Pat. No. 10,545,849.

(Continued)

(51) Int. Cl.
*G06F 11/36* (2006.01)
*H04W 4/70* (2018.01)
(Continued)

(52) U.S. Cl.
CPC ........ *G06F 11/3604* (2013.01); *A61B 5/6801* (2013.01); *G06F 8/65* (2013.01);
(Continued)

(58) Field of Classification Search
None
See application file for complete search history.

(56) References Cited

U.S. PATENT DOCUMENTS 7,792,922 B2 *   9/2010   Purcell .................... G06F 11/30
                                                  707/999.01
8,452,610 B2     5/2013   Lipner et al.
(Continued)

*Primary Examiner* — Duy Khuong T Nguyen
*Assistant Examiner* — Mark A Gooray
(74) *Attorney, Agent, or Firm* — Knobbe, Martens, Olson & Bear, LLP

(57) ABSTRACT

Disclosed are systems, methods, and articles for determining compatibility of a mobile application and operating system on a mobile device. In some aspects, a method includes receiving one or more data values from a mobile device having a mobile medical software application installed thereon, the data value(s) characterizing a version of the software application, a version of an operating system installed on the mobile device, and one or more attributes of the mobile device; determining whether the mobile medical software application is compatible with the operating system by at least comparing the received data value(s) to one or more test values in a configuration file; and sending a message to the mobile device based on the determining, the message causing the software application to operate in one or more of a normal mode, a safe mode, and a non-operational mode.

20 Claims, 9 Drawing Sheets

Related U.S. Application Data

(60) Provisional application No. 62/251,524, filed on Nov. 5, 2015.

(51) Int. Cl.

| | | |
|---|---|---|
| *G06F 8/71* | (2018.01) | |
| *G06F 8/70* | (2018.01) | |
| *G06F 11/14* | (2006.01) | |
| *G06F 11/00* | (2006.01) | |
| *G06F 9/445* | (2018.01) | |
| *G16H 40/40* | (2018.01) | |
| *H04L 29/08* | (2006.01) | |
| *H04W 4/20* | (2018.01) | |
| *G06F 8/65* | (2018.01) | |
| *H04M 1/725* | (2006.01) | |
| *H04W 4/12* | (2009.01) | |
| *A61B 5/00* | (2006.01) | |
| *H04W 88/02* | (2009.01) | |
| *A61B 5/145* | (2006.01) | |

(52) U.S. Cl.
CPC ............ *G06F 8/70* (2013.01); *G06F 8/71* (2013.01); *G06F 9/44505* (2013.01); *G06F 11/00* (2013.01); *G06F 11/143* (2013.01); *G06F 11/1433* (2013.01); *G06F 11/36* (2013.01); *G06F 11/3616* (2013.01); *G06F 11/3688* (2013.01); *G16H 40/40* (2018.01); *H04L 67/34* (2013.01); *H04M 1/72519* (2013.01); *H04W 4/12* (2013.01); *H04W 4/20* (2013.01); *H04W 4/70* (2018.02); *A61B 5/14532* (2013.01); *A61B 5/743* (2013.01); *H04M 1/72522* (2013.01); *H04W 88/02* (2013.01)

(56) References Cited

U.S. PATENT DOCUMENTS

| | | | |
|---|---|---|---|
| 8,595,607 B2 | 11/2013 | Nekoomaram et al. | |
| 9,336,353 B2* | 5/2016 | Valdes | G06F 19/3412 |
| 9,626,183 B1* | 4/2017 | Smith | G06F 9/44505 |
| 10,545,849 B2 | 1/2020 | Salameh et al. | |
| 2010/0313105 A1 | 12/2010 | Nekoomaram et al. | |
| 2011/0119072 A1 | 5/2011 | Lipner et al. | |
| 2012/0303476 A1 | 11/2012 | Krzyzanowski et al. | |
| 2013/0086573 A1* | 4/2013 | Moritzen | G06F 8/65 |
| | | | 717/171 |
| 2013/0132416 A1* | 5/2013 | Hayter | G06F 19/32 |
| | | | 707/758 |
| 2013/0317401 A1 | 11/2013 | Lee | |
| 2014/0012117 A1 | 1/2014 | Mensinger et al. | |
| 2015/0154364 A1 | 6/2015 | Biasi et al. | |
| 2017/0131993 A1 | 5/2017 | Salameh et al. | |

* cited by examiner

Non-Operation

The following core modules have been disabled.
- Module 1
- Module 2

Please visit www.URL1.com for more information and to obtain an update to the CGM application.

Safe Mode Operation

The following ancillary modules have been disabled:
- Module 3
- Module 4

Please visit www.URL2.com for more information regarding safe mode operation and to obtain an update to the CGM application.

COMPATIBILITY CHECK FOR CONTINUOUS GLUCOSE MONITORING APPLICATION

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/333,552, filed Oct. 25, 2016, which claims the benefit of U.S. Provisional Application No. 62/251,524, filed on Nov. 5, 2015. Each of the aforementioned applications is incorporated by reference herein in its entirety, and each is hereby expressly made a part of this specification.

TECHNICAL FIELD

The present disclosure generally relates to systems for managing continuous glucose monitoring medical devices and software compatibility between such devices and computer servers, and, more particularly, to determining whether a continuous glucose monitoring application installed on a user equipment is compatible with the user equipment's operating system.

BACKGROUND

Diabetes mellitus is a disorder in which the pancreas cannot create sufficient insulin. In a diabetic state, a person suffering from high blood sugar may experience an array of physiological side effects associated with the deterioration of small blood vessels. These side effects may include, for example, kidney failure, skin ulcers, bleeding into the vitreous of the eye, and the like. A hypoglycemic reaction, such as a low blood sugar event, may be induced by an inadvertent overdose of insulin, or after a normal dose of insulin or glucose-lowering agent. In a severe hypoglycemic reaction, there may be a high risk for headache, seizure, loss of consciousness, and coma.

A diabetic person may carry a self-monitoring blood glucose (SMBG) monitor which typically requires the user to prick his or her finger to measure his or her glucose levels. Given the inconvenience associated with traditional finger pricking methods, it is unlikely that a diabetic will take a timely SMBG measurement and, consequently, may be unaware whether his or her blood glucose value is indicative of a dangerous situation.

SUMMARY

Methods and apparatus, including computer program products, are provided for determining whether a user equipment's continuous glucose monitoring application and operating system are compatible.

In some example embodiments, there may be provided a method, which includes receiving, by at least one processor, one or more data values from a user equipment having a glucose monitoring application installed on the user equipment, the one or more data values characterizing a version of the glucose monitoring application, a version of an operating system installed on the user equipment, and one or more attributes of the user equipment; determining, by at least one processor, whether the glucose monitoring application is compatible with the operating system by at least comparing the received one or more data values to one or more test values in a configuration file, the one or more test values comprising one or more of a range of compatible operating system versions, a wildcard entry of compatible operating system versions, and a regular expression of compatible user equipment attributes; and sending, by at least one processor, a message to the user equipment based on the determining, the message causing the glucose monitoring application to operate in one or more of a normal mode, a safe mode, and a non-operational mode. Related systems, methods, and articles of manufacture are also disclosed.

In some example embodiments, one of more variations may be made as well as described in the detailed description below and/or as described in the following features. The one or more data values may be received from the user equipment when the glucose monitoring application is launched, when the glucose monitoring application is updated, when the glucose monitoring application is being used, or when the glucose monitoring application is idling. The one or more data values may be received from the user equipment, when the operating system is updated. The one or more data values may be received from the user equipment, when the user equipment is turned on or when the user equipment receives a request from a server communicatively coupled with the user equipment. The one or more attributes of the user equipment may include a manufacturer of the user equipment and a model of the user equipment. The message may cause the user equipment to display a user interface view on the user equipment while the glucose monitoring application is in the safe mode, the user interface view indicating that one or more ancillary functions are disabled. The one or more ancillary functions may include entering events associated with food consumption. The user interface view may indicate that an update for the glucose monitoring application is available. The message may cause the user equipment to display a user interface view on the user equipment while the glucose monitoring application is in the non-operational mode, the user interface view indicating that one or more core functions are disabled. The one or more core functions may include one or more of generating an alert, displaying a glucose level, and prompting calibration of a glucose sensor assembly. At least one processor may send the message a predetermined quantity of times while the glucose monitoring application is operating in the safe mode or the non-operational mode.

In some example embodiments, there may be provided a method, which includes receiving, by at least one processor, one or more data values from a user equipment having a glucose monitoring application installed on the user equipment, the one or more data values representing results from one or more self-tests performed on the user equipment, the one or more self-tests validating one or more features of one or more of the glucose monitoring application and the user equipment; determining, by at least one processor, whether the glucose monitoring application is compatible with the operating environment based at least on a comparison of the one or more data values with a predetermined list of self-tests; and sending, by at least one processor, a message to the user equipment based on the determining, the message causing the glucose monitoring application to operate in one or more of a normal mode, a safe mode, and a non-operational mode.

In some example embodiments, one of more variations may be made as well as described in the detailed description below and/or as described in the following features. The composite score may be a weighted sum of the one or more data values, an average of the one or more data values, a weighted average of the one or more data values, or a statistical mode of the one or more data values. The one or more self-tests may include one or more of a screenshot comparison self-test, a notification self-test, a layout self-test, a string self-test, a color comparison self-test, a user equipment state self-test, and a self-test of one or more systems of the user equipment. The one or more self-tests may be performed on the user equipment when the glucose monitoring application is launched, when the glucose monitoring application is updated, when the glucose monitoring application is being used, or when the glucose monitoring application is idling. The operating environment may include one or more of an operating system installed on the user equipment and an application which impacts operation of the glucose monitoring application. The one or more self-tests may be performed on the user equipment when the operating system is updated. The one or more self-tests may be performed on the user equipment when the user equipment is turned on or when the user equipment receives a request from a server communicatively coupled with the user equipment. The at least one processor may provide a script to the user equipment, the script causing the user equipment to perform the one or more self-tests. The one or more data values may be individually received after each of the one or more self-tests are performed or collectively received in a batch after all of the one or more self-tests are performed on the user equipment. The message may cause the user equipment to display a user interface view on the user equipment while the glucose monitoring application is in the safe mode, the user interface view indicating that one or more ancillary functions are disabled. The message may cause the user equipment to display a user interface view on the user equipment while the glucose monitoring application is in the non-operational mode, the user interface view indicating that one or more core functions are disabled.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

BRIEF DESCRIPTION OF THE DRAWINGS

The accompanying drawings, which are incorporated herein and constitute a part of this specification, show certain aspects of the subject matter disclosed herein and, together with the description, help explain some of the principles associated with the subject matter disclosed herein. In the drawings.

FIG. 6A illustrates a graphical user interface view associated with a non-operational mode, in accordance with some exemplary implementations;

FIG. 6B illustrates a graphical user interface view associated with a safe mode of operation, in accordance with some exemplary implementations;

Figure 1:
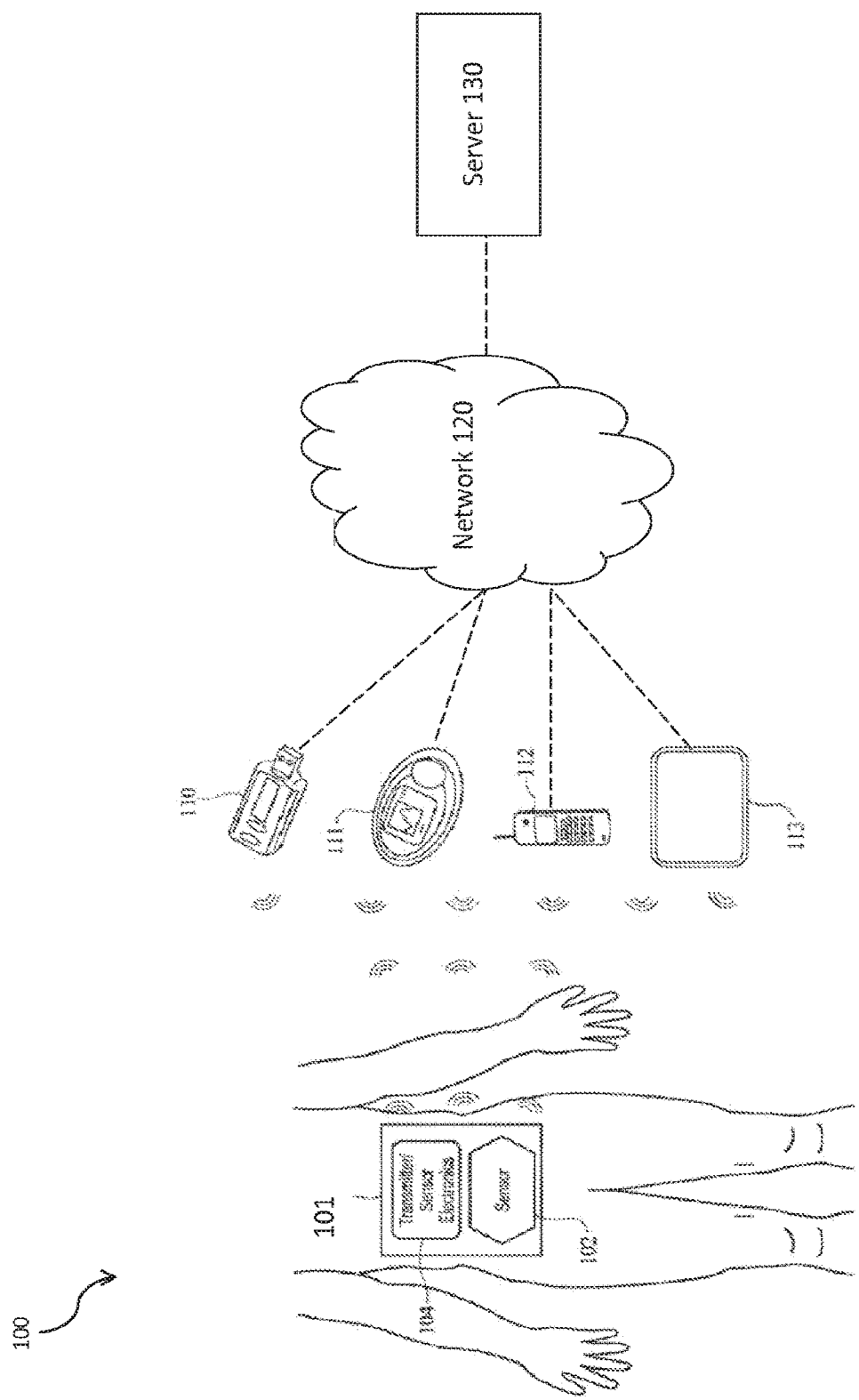
FIG. 1 illustrates a continuous analyte sensor system, in accordance with some exemplary implementations.

Like labels are used to refer to same or similar items in the drawings.

DETAILED DESCRIPTION

A variety of non-invasive, transdermal (e.g., transcutaneous) and/or implantable electrochemical sensors have been and are being developed for detecting and/or quantifying glucose values from such sensor measurements having accuracy corresponding to direct blood glucose measurements. These devices generally transmit raw or minimally processed data for subsequent presentation at a remote device, such as a patient's handheld computing device. A patient may use a mobile software application installed on the handheld computing device (i.e., an example of a user equipment) to check his/her glucose levels. Such software application may be considered or classified as a mobile medical application that meets a definition of a medical device. Proper operation of this mobile software application may warn the patient of a potential detrimental conditions, e.g., like a hypoglycemic reaction. Mobile medical applications are typically designed by a medical device entity to operate on a user's mobile communication or computing device, such as a smart phone or tablet, developed by another entity for non-medical related purposes.

Any changes or updates to a mobile medical application, such as a glucose monitoring application, or a user's handheld computing device's operating system may affect the operation of the application. For example, updates for the mobile application and the operating system may be developed by different entities and at different times, which creates a significant risk that updates to the software application and/or the operating system may be incompatible with each other or with other components within the mobile computing device (e.g., the mobile device's communication system, display system, and the like). Therefore, application incompatibility may adversely impact the operation of the mobile medical software application and any associated medical device apparatus. Consequently, there exists a need to ensure that the mobile medical application is compatible with the operating system of a user's mobile computing device.

Disclosed are systems and methods for determining whether mobile medical applications are compatible with an operating system installed on a mobile communications or computing device, such as a smart phone, tablet, or wearable computing device.

FIG. 1 is a schematic view of a continuous analyte sensor system 100 attached to a host and communicating with a number of example devices 110-113. A transcutaneous analyte sensor system includes an on-skin sensor assembly 101 that is fastened to the skin of a host via a disposable inserter or applicator (not shown). The system 100 includes a transcutaneous analyte sensor 102 and a transmitter/sensor electronics unit 104 for wirelessly transmitting analyte information to a receiver or receivers, such as devices 110-113. In alternative implementations, the sensor may be non-invasive.

During use, a sensing portion of the sensor 102 is under the host's skin, and a contact portion of the sensor 102 is electrically connected to the electronics unit 104. The electronics unit 104 engages a housing of the on-skin sensor assembly 101 (not shown), and the sensor extends through the housing. The housing, which maintains the assembly 101 on the skin and provides for electrical connection of the sensor 102 to sensor electronics provided in the electronics unit 104, is attached to an adhesive patch (not shown) fastened to the skin of the host.

The on-skin sensor assembly 101 may be attached to the host with an applicator (not shown) adapted to provide convenient and secure application. Such an applicator may also be used for attaching the electronics unit 104 to the housing of the on-skin sensor assembly 101, inserting the sensor 102 through the host's skin, and/or connecting the sensor 102 to the electronics unit 104. Once the electronics unit 104 is engaged with the housing and the sensor 102 has been inserted and is connected to the electronics unit 104, the applicator detaches from the sensor assembly.

In general, the continuous analyte sensor system 100 includes any sensor configuration that provides an output signal indicative of a concentration of an analyte. The output signal, which may be in the form of, for example, sensor data, such as a raw data stream, filtered data, smoothed data, and/or otherwise transformed sensor data, is sent to the receiver, which is described in more detail below. In various implementations, the analyte sensor system 100 includes a transcutaneous glucose sensor, a subcutaneous glucose sensor, a continuous refillable subcutaneous glucose sensor, or a continuous intravascular glucose sensor, for example.

In some implementations, the sensor 102 extends through a housing (not shown), which maintains the sensor on the skin and provides for electrical connection of the sensor to sensor electronics, provided in the electronics unit 104. In various implementations, the sensor 102 is formed from a wire. For example, the sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some implementations the smallest dimension of the elongated conductive body is less than about 0.1 inches, 0.075 inches, 0.05 inches, 0.025 inches, 0.01 inches, 0.004 inches, or 0.002 inches, albeit other dimensions of the conductive body can be used. Preferably, a membrane system is deposited over at least a portion of electroactive surfaces of the sensor 102 (including a working electrode and optionally a reference electrode) and provides protection of the exposed electrode surface from the biological environment, diffusion resistance (limitation) of the analyte if needed, a catalyst for enabling an enzymatic reaction, limitation or blocking of interferents, and/or hydrophilicity at the electrochemically reactive surfaces of the sensor interface.

In general, the membrane system includes a plurality of domains, for example, an electrode domain, an interference domain, an enzyme domain (for example, including glucose oxidase), and a resistance domain, and can include a high oxygen solubility domain, and/or a bioprotective domain. The membrane system may be deposited on the exposed electroactive surfaces using known thin film techniques (for example, spraying, electro-depositing, dipping, etc.). In various implementations, one or more domains are deposited by dipping the sensor into a solution and drawing out the sensor at a speed that provides the appropriate domain thickness. However, the membrane system can be disposed over (or deposited on) the electroactive surfaces using any known method.

In the illustrated implementation, the electronics unit 104 is releasably attachable to the sensor 102, which together form the on-skin sensor assembly 101. The electronics unit 104 includes electronic circuitry associated with measuring and processing the continuous analyte sensor data, and is configured to perform algorithms associated with processing and calibration of the sensor data. The electronics unit 104 may include hardware, firmware, and/or software that enable measurement of levels of the analyte via the analyte sensor 102, e.g., such as glucose levels in embodiments of the analyte sensor 102 as a glucose sensor. For example, the electronics unit 104 can include a potentiostat, a power source for providing power to the sensor 102, other components useful for signal processing and data storage, and preferably a telemetry module for one- or two-way data communication between the electronics unit 104 and one or more receivers, repeaters, and/or display devices, such as the devices 110-113. Sensor electronics within the electronics unit 104 can be affixed to a printed circuit board (PCB), etc., and can take a variety of forms. For example, the electronics can take the form of an integrated circuit (IC), such as an application-specific integrated circuit (ASIC), a microcontroller, and/or a processor. The electronics unit 104 may include sensor electronics that are configured to process sensor information, such as storing data, analyzing data streams, calibrating analyte sensor data, estimating analyte values, comparing estimated analyte values with time corresponding measured analyte values, analyzing a variation of estimated analyte values, such as estimated glucose values (EGVs), etc.

The devices 110-113 may operate as repeaters, receivers, and/or display devices (also referred to herein more generally as "receivers" or "CGM receivers"). In the example of FIG. 1, device 110 comprises a key fob repeater 110, device 111 comprises a dedicated medical device receiver 111, device 112 comprises a smart phone 112 including an application 1351) (e.g., such as a CGM application) to provide the receiver disclosed herein, and device 113 comprises a portable or tablet computer 113 including an application 135C (e.g., such as a CGM application) to provide the receiver disclosed herein; although other types of devices capable of receiving, repeating, and/or displaying the analyte sensor data provided by electronics unit 104 may be used as well. One or more of a key fob repeater 110, a medical device receiver 111, a smart phone 112, a portable or tablet computer 113, etc. are operatively linked (e.g., via wireless link(s)) to the electronics unit 104.

These display devices 110-113 can receive data from the electronics unit 104, which is also referred to as the transmitter and/or sensor electronics body herein. In some implementations the repeaters, receivers and/or display devices transmit data to the electronics unit 104. For example, the sensor data can be transmitted from the sensor electronics unit 104 to one or more of the key fob repeater 110, the medical device receiver 111, the smart phone 112, the portable or tablet computer 113, etc.

Also, in some implementations the repeaters, receivers and/or display devices may transmit data to one another or to a remote server 130 through a wireless connection or a wired connection via network 120. The remote server 130 may have at least one processor and at least one memory storage device, such as a database, that stores and processes data received from one or more of the key fob repeater 110, the medical device receiver 111, the smart phone 112, the portable or tablet computer 113. For example, the medical device receiver 111 may receive analyte data such as CGM data from the transmitter 104. Medical device receiver 111 may display the CGM data as well as related alerts and the like. Medical device receiver 111 may also provide the CGM data to other devices, such devices 110, 112, 113, as well as one or more other servers, such as the remote server 130, via for example network 120 and/or directly through wired or wireless communications. Similarly, for example, smart phone 112 may receive the CGM data directly from the transmitter 104. Smart phone 112 can display the CGM data as well as related alerts and the like, as well as may also provide the CGM data to other devices, such as the devices 110, 113, or wearable devices like a smart watch or smart glasses connected to the smart phone 112, as well as one or more other servers, such as secure server 130, via for example network 120 and/or directly through wired or wireless communications.

In various implementations, a display device includes an input module with a quartz crystal operably connected to a radio-frequency (RF) transceiver (not shown) that together function to transmit, receive and synchronize data streams from the electronics unit 104 and/or a continuous glucose monitor (CGM). However, the input module can be configured in any manner that is capable of receiving data from the electronics unit 104 and/or the CGM. Once the data stream is received, the input module sends it to a processor that processes the data stream, such as described in more detail below. The processor may be internal or external to the display device. For example, the input module may send some or all of the data to a remote processor, such as a processor in the cloud (described further below). The remote processor may then send the processed data back to the input module, or store it remotely. The processor is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, etc. The processor includes hardware that performs the processing described herein. Storage provides permanent or semi-permanent storage of data, storing data such as a sensor ID, a receiver and programming to process data streams (for example, programming for performing estimation and other algorithms described elsewhere herein). Random access memory (RAM) stores the system's cache memory and is used in data processing. An output module, which may be integral with and/or operatively connected with the processor, includes programming for generating output based on the data received from the electronics unit 104 and/or the CGM (and any processing incurred in the processor).

In some implementations, analyte values are displayed on any of display devices 110-113. In some implementations, prompts or messages can be displayed on the display device to convey information to the user, such as reference outlier values, requests for reference analyte values, therapy recommendations, deviation of the measured analyte values from the estimated analyte values, etc. Additionally, prompts can be displayed to guide the user through calibration or troubleshooting of the calibration.

Additionally, data output from the output module can provide wired or wireless, one- or two-way communication between the display device and an external device. The external device can be any device that interfaces or communicates with the receiver. In some implementations, the external device is a computer, and the receiver is able to download current and/or historical data for retrospective analysis by a physician, for example. In some implementations, the external device is a modem, and the receiver is able to send alerts, warnings, emergency messages, etc., via telecommunication lines to another party, such as a doctor and/or a family member. In some implementations, the external device is an insulin pen or insulin pump, and the receiver is able to communicate therapy recommendations, such as an insulin amount and a time to the insulin pen or insulin pump. The external device can include other technology or medical devices, for example pacemakers, implanted analyte sensor patches, other infusion devices, telemetry devices, etc.

The receiver may communicate with the external device, and/or any number of additional external devices, via any suitable communication protocol, including radio frequency (RF), Bluetooth, universal serial bus (USB), any of the wireless local area network (WLAN) communication standards, including the IEEE 802.11, 802.15, 802.20, 802.22 and other 802 communication protocols, ZigBee, wireless (e.g., cellular) telecommunication, paging network communication, magnetic induction, satellite data communication, GPRS, ANT, 3G, 4G, 5G, LTE, and/or a proprietary communication protocol.

Figure 2:
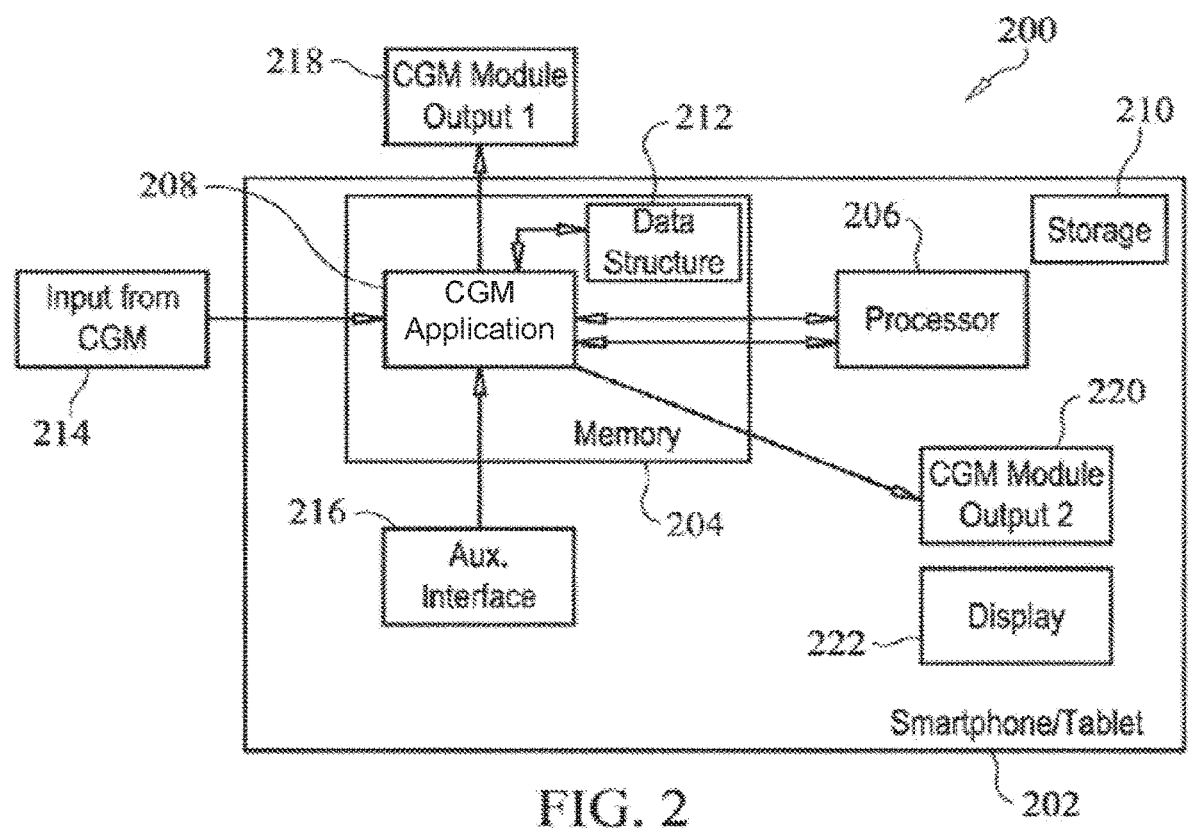
FIG. 2 illustrates a functional block diagram of a mobile device/user equipment used with a continuous analyte sensor system, in accordance with some exemplary implementations.

FIG. 2 is a functional block diagram of one implementation of a system 200 for leveraging mobile device features in continuous analyte monitoring, such as continuous glucose monitoring, according to the present implementations. The system 200 includes a mobile device or user equipment 202 which may be any type of computing device capable of receiving one or more inputs and producing an output, such as a smartphone, a tablet computing device, a laptop, a wearable computing device, and/or the like. User equipment 202 can, for example, correspond to any of display devices 110-113. The instant disclosure uses the terms mobile device and user equipment interchangeably.

The mobile device or user equipment 202 may include a memory 204 and a processor 206. The memory 204 may provide the processor 206 access to data and program information that is stored in the memory 204 at execution time. Typically, the memory 204 may include random access memory (RAM) circuits, read-only memory (ROM), flash memory, etc., or a combination of such devices. The processor 206 may be, or may include, one or more programmable general-purpose or special-purpose microprocessors, digital signal processors (DSPs), programmable controllers, application specific integrated circuits (ASICs), programmable logic devices (PLDs), etc., or a combination of such hardware-based devices.

In accordance with the present implementations, the processor 206 may execute a continuous glucose monitoring (CGM) application 208 out of the memory 204. The CGM application 208 may perform other functions besides monitoring glucose. For example, the CGM application 208 can communicate with insulin delivery therapies, such as insulin pumps, and determine that a user's glucose level is high, and then transmit a signal to the user's insulin pump to administer a quantity of insulin to bring the user's glucose level down.

A software and/or firmware component of the CGM application 208 may be stored in storage 210 available to the mobile device 202, and loaded into the memory 204 at execution time. The storage 210 may be any non-transitory computer readable media including, but not limited to, a hard disk, EEPROM (electrically erasable programmable read only memory), a memory stick, or any other storage device type. The memory 204 may contain one or more data, structures 212 that the CGM application 208 accesses during execution. For example, the CGM application 208 may receive an input and store the input as an input parameter in a data structure 212 in the memory 204 for later processing.

In certain implementations, the CGM application 208 may be embodied as downloadable software that a user may download from a remote server through a wired or wireless connection. For example, the user may access the server using an application already installed on the user's mobile device. The user may then download and install the CGM application 208 with the aid of the application. If, for example, the user is using an iPhone mobile phone, he/she can download the CGM application 208 from the iTunes store. In another example, if the user is using an Android mobile phone, he/she can download the CGM application 208 from Google Play. The user may then configure the CGM application 208. For example, the configuration may include setting the user's personal preferences and/or settings, such as contacts, events, modes, profiles, etc. The configuration may be done manually, such as by selecting various options from menus, or automatically. In automatic configuration, the CGM application 208 reads the user's preferences and/or settings that are stored on the mobile device 202. For example, in some implementations, the CGM application 208 would first discover what other applications are installed on the mobile device, and then access those applications' data stored in the mobile device's storage and/or remote storage accessible by the mobile device 202 to initially populate the CGM application 208 during set up. For example, a health application may be installed on mobile device 202 that tracks the user's resting heart rate, blood pressure, weight, height, and the like. The CGM application 208 may import data from the health application directly into the CGM application 208 for later use.

In some implementations, the CGM application 208 operating on the mobile device 202 receives at least one input 214 from the CGM transmitter or other device, such as devices 110-113. For example, the input can include a current EGV for the patient or user input by and/or about the patient. In some implementations, the CGM application 208 receives input from an auxiliary interface 216. The auxiliary interface 216 may be any of hardware, software, firmware, or a combination of any of these, and may comprise anything that may be combined with EGV data and processed to produce an output that can provide the user with information that can help him or her make more informed decisions about how to manage his or her glucose. In some embodiments, for example, the auxiliary interface 216 may be a sensor, which may be internal or external to the mobile device 202, or may be another application executed by the mobile device 202.

In some implementations of the system 200, the CGM application 208 operating on the mobile device 202 processes the inputs in conjunction with the processor 206 to produce one or more outputs 218, 220. For example, the output 218 may be to a device or receiver external to the mobile device 202 (shown as CGM Module Output 1, 218, in FIG. 2), or to a device internal to the mobile device 202 (shown CGM Module Output 2, 220), such as to a display 222 or storage 210.

Figure 3:
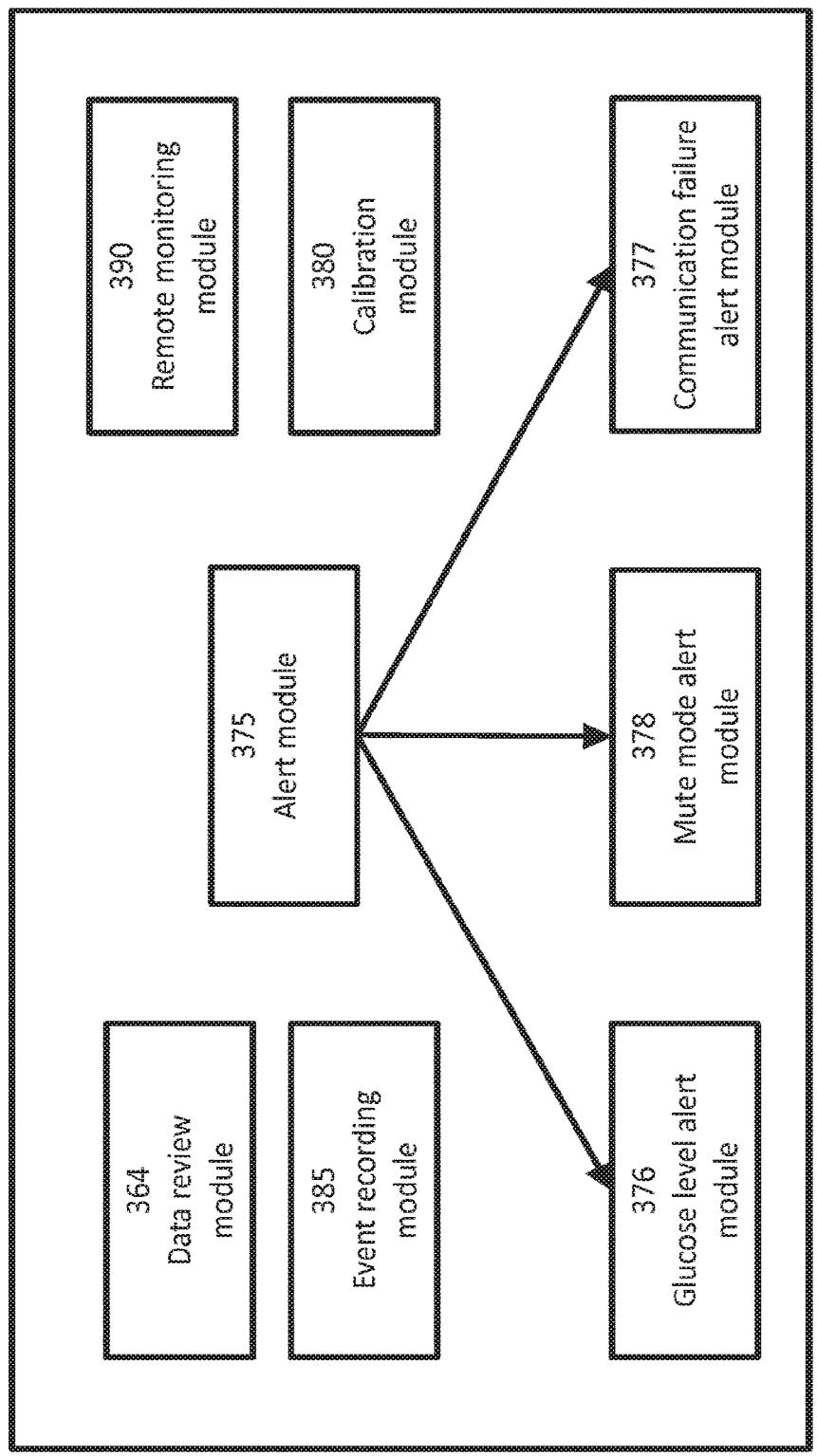
FIG. 3 illustrates a functional block diagram of a continuous glucose monitoring (CGM) application, in accordance with some exemplary implementations.

FIG. 3 illustrates a functional block diagram of the CGM application 208 running on mobile device 202. This block diagram includes various software modules or features that control the behavior of the CGM application 208. The software modules and features of CGM application 208 may include a data review module 364, an event recording module 385, a remote monitoring module 390, a calibration module 380, and an alert module 375. Each of these modules is described below.

Data review module 364 may display a patient's glucose levels. The data review module 364 may provide information regarding a patient's current glucose level and its rate of change. Data review module 364 may also display a graph of the patient's glucose data over time, e.g., which may be referred to as a trend graph, that illustrates variations in a patient's glucose level over time and may indicate the presence of a clinical risk to the patient.

Remote monitoring module 390 may share a patient's glucose level information with other users, such as one or more remote monitors. A server, such as server 130, may push this information to secondary computing devices. A patient may use remote monitoring module 290 to invite remote monitors to receive this information and customize the type of information that may be provided to and/or viewed by invited remote monitors.

A patient may use event recording module 385 to enter and recall events. Events may include food intake, medication intake, exercise, and the like. By recording this information, the patient may obtain a better understanding of how different types of events may influence his/her glucose levels.

Calibration module 380 may calibrate glucose data measurements received from sensor assembly 101. The calibration module 380 can manage how user-inputted calibration data is transmitted to the sensor assembly 101. The calibration module 380 may alert a user when calibration measurements are needed.

Alert module 375 may generate various alarms or alerts using glucose level alert module 376, mute mode alert module 378, and communication failure alert module 377. Glucose level alert module 376 may be a sub-module of alert module 375 and may be configured to generate an alarm if a patient's glucose level drops below or rises above a predetermined threshold value. For example, a patient may use alert module 375 to set alerts for different parameters or circumstances. Also, in some embodiments, for example, a patient may use the alert module 375 to designate which alerts to propagate to the remote monitors, e.g., via the remote monitoring module 390. Mute mode alert module 378 may be a sub-module of alert module 375 and may be configured to alert a patient if the patient's mobile device 202 is determined to be muted. Because a patient may not hear any alerts when his or her mobile device 202 is muted, mute mode alert module 378 may initiate one or more remedial actions, such as propagating one or more alerts to remote monitors. Communication failure alert module 377 may be a sub-module of alert module 375 and may be configured to alert a patient or remote follower if application 208 is determined to be terminated. This notification may prompt the patient to reboot or relaunch application 208 so that he or she may continue receiving glucose level data from sensor system 100.

A user may download updates to mobile device 202 that can impact the operation of CGM application 208. These updates can be designed for CGM application 208 or for an operating system installed on mobile device 202. With regard to CGM application updates, mobile device 202 may download software updates for CGM application 208 from server 130. In some implementations, for example, downloaded software updates for CGM application 208 from server 130 may be routed through one or more other servers and/or services, e.g., such as through Apple® App or iTunes Store or Google Play. These software updates may correct technical issues associated with CGM application 208 and its various modules. For example, if a software error is found in alert module 375, then the error may be corrected by downloading and installing an update for CGM application 208. Software updates may also provide new functionality for CGM application 208 (e.g., the addition of new modules), enhance background processes (e.g., security updates), and the like.

With regard to operating system updates, mobile device 202 may download operating system updates that can correct or enhance the operation of the operating system and/or the mobile device. These operating system updates may, for example, provide improved power savings or memory allocation techniques. Because updates for the CGM application 208 and the operating system may be developed by different entities, there is a risk that updates to the CGM application and/or the operating system may be incompatible with each other or with other components within the mobile device (e.g., the mobile device's communication system, display system, and the like). Application incompatibility may adversely impact the operation of CGM application 208. For example, if a user has downloaded an operating system update that deactivates alert module 375, then CGM application 208 may be unable to generate alerts. The presence of other applications may also impact the operation of the CGM application 208. For example, if the user is using a multimedia application to watch a movie on mobile device 202, the multimedia application may mute sounds from all other applications on the mobile device, including alert module 375 in the CGM application 208. This consequence may be dangerous if, for example, a user's glucose level drops. Because an alert may not be received by mobile device 202, the user may be unaware of a potentially dangerous hypoglycemic reaction.

Figure 4:
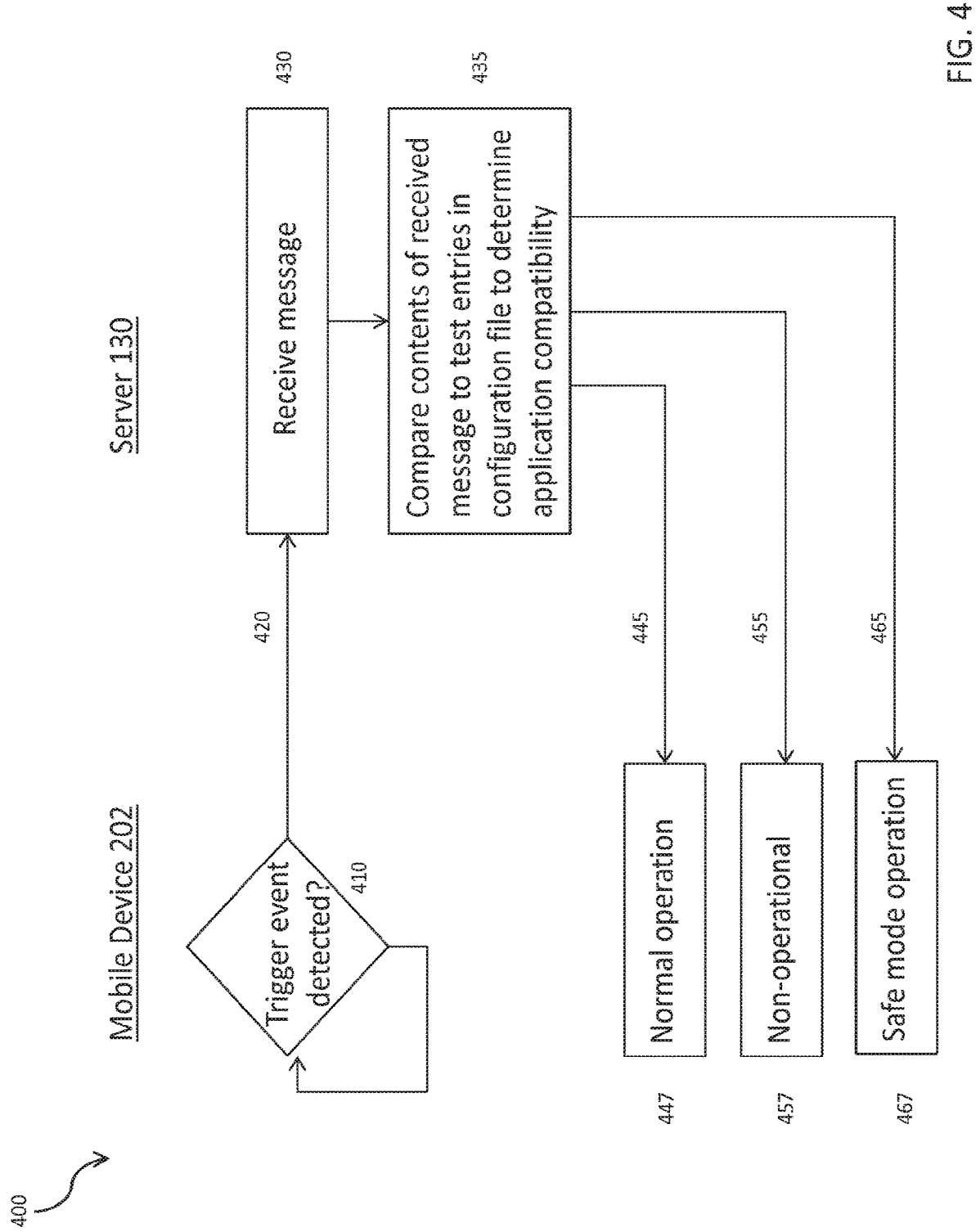
FIG. 4 illustrates a flowchart for determining CGM application compatibility, in accordance with some exemplary implementations.
Figure 5:
FIG. 5 illustrates a configuration file, in accordance with some exemplary implementations.
Figure 7:
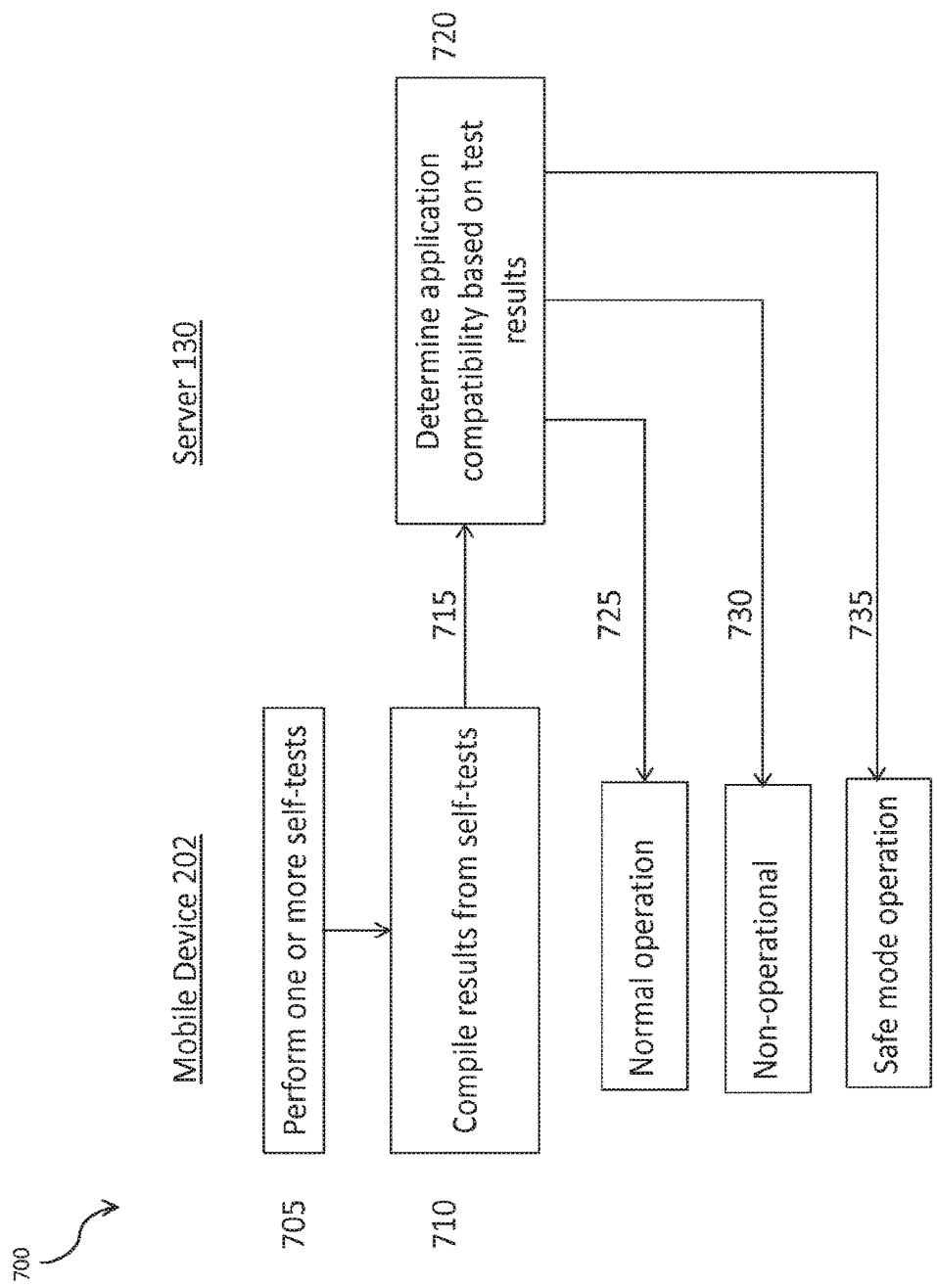
FIG. 7 illustrates a flowchart for performing self-tests and determining application compatibility based on the self-tests, in accordance with some exemplary implementations.
Figure 8:
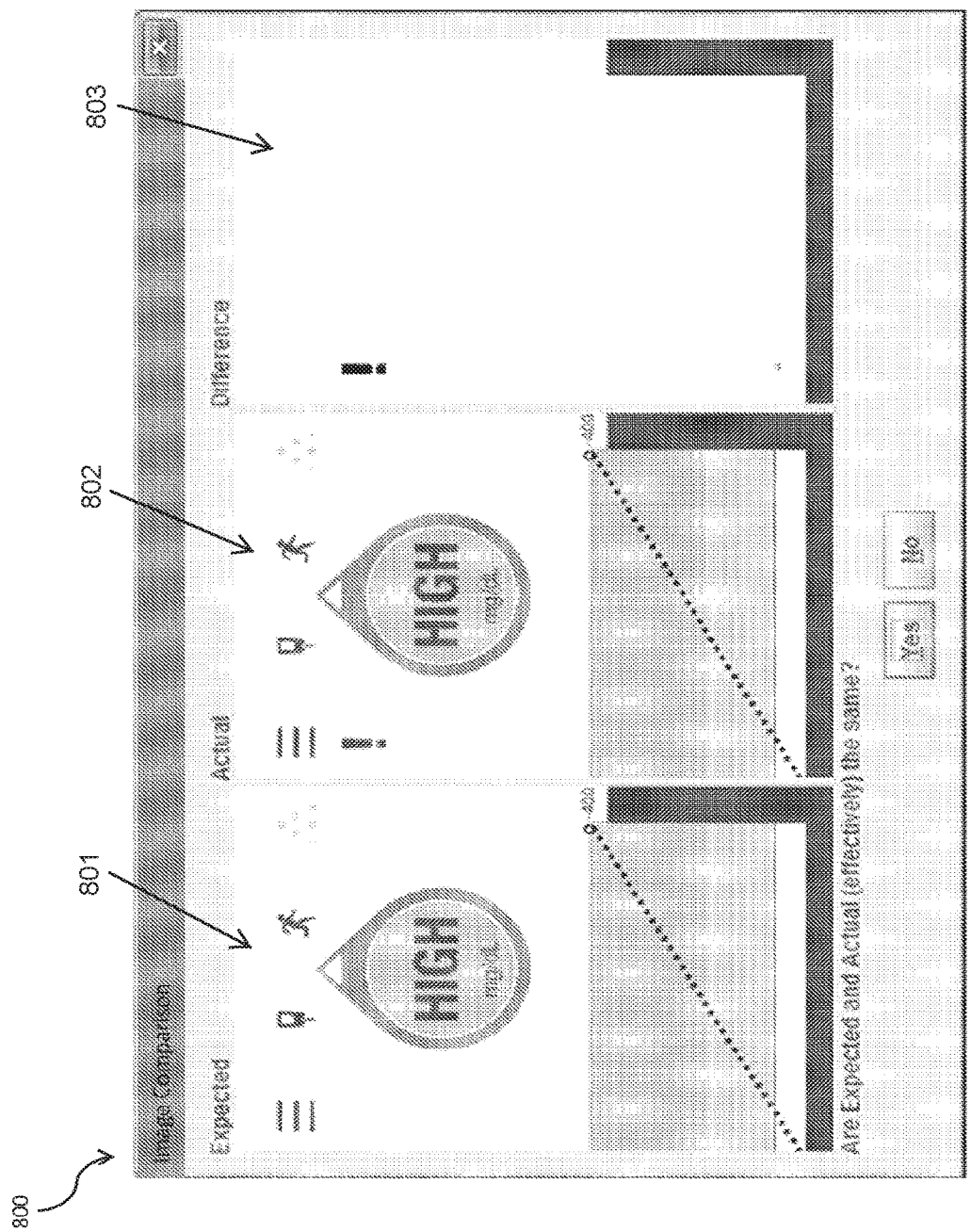
FIG. 8 illustrates a graphical user interface view for performing a screenshot comparison self-test, in accordance with some exemplary implementations.
Figure 9:
FIG. 9 illustrates a graphical user interface view for performing a string self-test, in accordance with some exemplary implementations.

Example embodiments of the systems and techniques of the present technology for determining compatibility between a mobile medical application and an operating system installed on a mobile device. Although these techniques are primarily described with respect to CGM application 208 and the mobile device's operating system, these techniques may also determine compatibility between the CGM application and other components or functions of the mobile device including, for example, the mobile device's communication system, the mobile device's display system, the mobile device's audio system, other applications installed on the mobile device, and the like. Application compatibility may be determined by server 130, by mobile device 202, or both. In the implementations of FIGS. 4-6, server 130 may determine application compatibility based on device related information received from mobile device 202. In the implementations of FIGS. 7-9, mobile device 202 may perform various self-tests and report the results of these self-tests to server 130 to facilitate this determination.

FIG. 4 illustrates a flowchart 400 for determining compatibility between a mobile medical application and an operating system installed on a mobile device, such as CGM application 208 and the operating system of mobile device 202. Server 130 may make this determination using information provided by mobile device 202. At 410, mobile device 202 may determine whether a trigger event has been detected at the mobile device. A trigger event may be an event that initiates the compatibility verification process. A trigger event may occur, for example, when CGM application 208 is launched on mobile device 202, when the CGM application 208 is upgraded or updated, while the CGM application 208 is being used, while the CGM application 208 is idling in the background of the mobile device 202, when the operating system on the mobile device 202 has been upgraded or updated, when the mobile device 202 is turned on, e.g., upon receiving a request from server 130 or an operator of the mobile device 202, on a periodic basis (e.g., once an hour, once a day, or once a week), and the like. If a trigger event is detected, then mobile device 202 may transmit a message at 420 indicating the same to server 130.

The message transmitted at 420 may include one or more data values characterizing the mobile device 202, the trigger event, and the like. Data values associated with mobile device 202 may include, for example, an identity of the mobile device (e.g., SIM card identifier), one or more values identifying CGM application 208 (e.g., a version number, an upgrade history, a mode of operation (e.g., blinded mode or unblinded mode), etc.), one or more values identifying an operating system installed on the mobile device (e.g., the operating system's name, version number, upgrade history, etc.), and the like. Data values associated with the trigger event may include, for example, a description of the detected trigger event, when the trigger event occurred, and the like. Server 130 may receive this message and its corresponding data values at 430.

At 435, server 130 may determine CGM application compatibility by comparing the data values received at 430 with one or more test entries in a configuration file. The test entries may correspond to different combinations of mobile devices and operating systems that have been previously tested with CGM application 208. As such, the test entries in the configuration file may identify which combinations of mobile devices and operating systems are compatible with CGM application 208. Because CGM application 208 may be designed to work with a large number of mobile device and operating system combinations, the contents of the configuration file may be large. The number of test entries in the configuration file may increase as new mobile devices are brought to market and new updates for the CGM application 208 and the operating system are released.

Having a large configuration file, however, may be difficult to maintain. For example, when a new operating system update is released (e.g., Android® 5.0), a large number of compatibility tests may be needed for mobile devices that use the operating system (e.g., existing Samsung®, Motorola®, and HTC® mobile devices). Manually updating the configuration file with test results from each mobile device/operating system combination may be time consuming and error prone. These long update times may also lead to server downtime while a new configuration file is uploaded to server 130. In order to remedy these deficiencies, the subject matter disclosed herein provide techniques for reducing the size of the configuration file using truncated test entry values, as described below with respect to FIG. 5.

FIG. 5 illustrates an exemplary implementation of a configuration file 500. This file may be locally saved to a memory storage device at server 130 or remotely accessed by the server. Configuration file 500 may include one or more test entries 540, 542, 544, 550, and 552. Each test entry may correspond to a different test combination of CGM application 208 with a particular mobile device 202 and its operating system. Configuration file 500 may include information regarding the tested CGM application version number 510, a mobile device or user equipment manufacturer 515 (e.g., Samsung®), a mobile device or user equipment model name 520 (e.g., Galaxy S6), an operating system name 525 (e.g., Android®), and an operating system version number 530 (e.g., 5.0.2). Test entries 540, 542, and 544, for example, identify all mobile devices and operating systems that are either fully compatible or partially compatible with CGM application version number 1.0, as indicated by compatibility column 535. Similarly, test entries 550 and 552 identify all mobile devices and operating systems that are incompatible or fully compatible with CGM application version number 2.0, as indicated by compatibility column 535.

As described above, configuration file 500 may include truncated test entries in order to reduce the size of the configuration file. Various types of truncation may be used including, for example, ranges of values, wildcard entries, regular expressions, and the like. Each type of truncation is described below.

A range may include a set of different values of the same type. Rather than specify each individual value, which may consume unnecessary space in configuration file 500, a range of values may represent the same using only two values (i.e., a low and a high value). For example, test entry 540 may include a range of operating system version numbers 1.0-1.5. This range may include operating system version numbers 1.0, 1.5, and any intermediate version numbers (e.g., 1.0.5, 1.1, 1.4.2, and the like).

A wildcard entry may include a symbol that can take on any value. Using a wildcard entry may obviate the need to specify low and high values associated with a range which, in turn, may reduce the number of characters needed to identify a range. For example, test entry 550 may have a wildcard entry (3.*) in operating system version number field 530. Because the symbol, *, may take on any value, this wildcard entry may include operating system version numbers 3.0 through 3.9. In some instances, a wildcard entry may be used in combination with a range. For example, test entry 552 may have a range of operating system version numbers 3.*-4.*. This range can include version numbers 3.0 through 4.9.

A regular expression may include a sequence of characters that may be used to match test entry values. Regular expressions may use metacharacters to help delimit the search, as generally known in the art. Test entry 544, for example, may include a regular expression, .*, in the device name field 520 and in the operating system version number field 530. Using .* as a regular expression may return matches having 0 or more occurrences of any character (i.e., any device name value will result in a match).

Returning to process 435, server 130 may determine whether the mobile device 202's CGM application 208 and operating system are compatible with each other by comparing the received message (e.g., content of the message including data values) with the test entries in configuration file 500. This determination may yield three possible results—full compatibility (which may result in normal operation 447), incompatibility (which may result in a non-operational mode 457), and partial compatibility (which may result in safe mode operation 467). Each scenario is described below.

CGM application 208 may be fully compatible with an operating system when all of the functions in the CGM application are operational. In an illustrative example with respect to FIGS. 4 and 5, if the message received at 430 indicates that a user is running CGM application version 1.0 on an Acme phone_2 installed with version 2.1 of the Avalanche operating system, then server 130 compares these data values to the test entries in configuration file 500. Upon doing so, server 130 determines, in this example, that this particular combination of data values, which corresponds to data entry 542, indicates the result of full compatibility, i.e., the version of the CGM application 208 is fully compatible with the mobile device 202's operating system, as indicated by column 535 of FIG. 5. Upon making this determination, server 130 transmits a message at 445 of FIG. 4 to mobile device 202 indicating full compatibility. For example, because CGM application 208 is fully compatible with the operating system, all of the example CGM application modules described above with respect to FIG. 3 are available to the user. Upon receiving this message, CGM application 208 may operate in a normal manner according to its expected use.

CGM application 208 may be incompatible with an operating system when one or more core functions of the CGM application 208 are not operational or disabled. A core function may include any module that is essential to the operation of CGM application 208. Disabling a core function may, in some scenarios, result in a life threatening condition. For example, if alert module 375 (or any of alert submodules 376, 377, and 378) is disabled, then a user may not receive any alerts relating to his/her glucose level. If the user experiences a drop in glucose level but fails to receive any alerts, the user may develop a potentially fatal hypoglycemic reaction. For example, the data review module 364 may be another core function. As described above, data review module 364 displays a patient's glucose level. Disabling data review module 364 may interfere with the patient's ability to determine whether his/her glucose level is low, normal, or high. In yet another example, calibration module 380 may be another core function. If, for example, calibration module 380 is disabled, then a user may not be prompted to recalibrate sensor assembly 101. Failure to recalibrate sensor assembly 101 may result in skewed glucose measurements which, in turn, may affect alert generation.

Referring again to FIG. 4 in another illustrative example, if the message received at 430 indicates that a user is running CGM application version 2.0 on an Acme phone_2 installed with version 3.0 of the Avalanche operating system, then server 130 compares these data values to the test entries in configuration file 500. Upon doing so, server 130, in this example, determines that this particular combination of data values, which corresponds to data entry 550, indicates the result of incompatibility, i.e., this version of CGM application 208 may be incompatible with the mobile device 202's operating system, as indicated by column 535 of FIG. 5. Upon making this determination, server 130 transmits a message at 455 of FIG. 4 to mobile device 202 indicating the same. For example, because the CGM application 208 is incompatible with the operating system, one or more of the CGM application's core functions may be disabled by one or more of the mobile device 202 and the CGM application 208. Upon receiving this message, CGM application 208 may become non-operational and all functions associated with the CGM application may be turned off.

In some implementations, CGM application 208 may display graphical user interface view 600 in FIG. 6A upon entering this non-operational mode. Graphical user interface view 600 may display a message indicating that one or more core modules or functions associated with CGM application 208 have been disabled. Graphical user interface view 600 may also direct the user to one or more resources (e.g., a website address) for obtaining any available CGM application updates.

CGM application 208 may be partially compatible with an operating system when one or more ancillary functions of the CGM application are disabled. An ancillary function may include any module that is not essential to the operation of CGM application 208 and/or does not significantly impact safety to the patient. Disabling an ancillary function may not lead to a life threatening condition. Referring to FIG. 3, event recording module 385 may be an ancillary function. As described above, a user may utilize event recording module 385 to record the consumption of food and/or drinks. This information may be used to determine how the user's diet affects his/her glucose level. While event recording module 385 provides useful information, its operation is not essential to CGM application 208 and may be disabled without leading to a life threatening situation, for example.

Referring again to FIG. 4 in another illustrative example, if the message received at 430 indicates that a user is running CGM application version 1.0 on an Acme phone_1 installed with version 1.3 of the Avalanche operating system, then server 130 compares these data values to the test entries in configuration file 500. Upon doing so, server 130, in this example, determines that this particular combination of data values, which corresponds to data entry 540, indicates the result of incompatibility, i.e., this version of CGM application 208 may be partially compatible with the mobile device's operating system, as indicated by column 535 of FIG. 5. Upon making this determination, server 130 transmits a message at 465 of FIG. 4 to mobile device 202 indicating the same. For example, because the CGM application 208 is partially compatible with the operating system, one or more of the CGM application's ancillary functionality may be disabled by one or more of the mobile device 202 and the CGM application 208. Doing so may cause the CGM application 208 to operate in a safe mode.

In some implementations, CGM application 208 may display graphical user interface view 620 in FIG. 6B upon entering safe mode. Graphical user interface view 620 may display a message that identifies which ancillary modules have been disabled. Graphical user interface view 620 may also direct the user to one or more resources (e.g., a website address) for obtaining more information about safe mode operation and any available CGM application updates.

In order to encourage the user to take action and resolve any compatibility issues, server 130 may warn the user of the same. In some implementations, server 130 warns the user by sending messages 455 and 465 multiple times. Upon receiving these messages, mobile device 202 can display graphical user interface views 600 and 620, for example. Repeated display of graphical user interface views 600 and 620 may encourage a user to download any available application updates. Sever 130 may be configured to send messages 455 and 465 a predetermined quantity of times at predetermined intervals or until full compatibility is achieved.

In some implementations, the configuration file can include information regarding the transmitter 104. In an illustrative example, the transmitter 104 may be operating on a particular version of firmware (e.g., Tx v1.2 firmware) for a particular hardware version of the transmitter 104. The transmitter 104 can thus provide transmitter identification information, e.g., including the firmware version and/or transmitter version, in advertisements transmitted by the transmitter 104 to the receiver 110-113, e.g., such as mobile device 201 operating the CGM application 208. In some situations, compatibility problems can occur where the transmitter 104 may only be compatible with certain configurations of the user's mobile device 202, such as the particular smart phone device and/or version of the operating system running on that particular smart phone device. Therefore, by including the transmitter identification information, e.g., such as the version number and the software version number in the advertisement packet from the transmitter 104 to the mobile device 202, the transmitter identification information can be included in the message and provided in the configuration file. In this regard, the compatibility check can include compatibility of a complete medical device that includes a sensor device, e.g., sensor assembly 101, and the mobile medical application, e.g., CGM application 208, with the user equipment, e.g., mobile device 202 such as a user's smart phone. In some implementations, if incompatibility is determined based on the transmitter identification information, the mobile device 202 may not attempt to further connect with the transmitter 104 and/or can display a message to the user on the mobile device 202 that the mobile device 202 and transmitter 104 are incompatible.

In some implementations, determination of CGM application compatibility may be based on self-tests performed by the mobile device 202, e.g., the user equipment. These self-tests may test different features of CGM application 208 and/or user equipment in order to validate that the application is working properly. The results of these self-tests may provide useful information regarding the CGM application 208 that the server 130 may be unaware of. These tests may verify, for example, whether graphical user interface views are properly displayed, whether notifications are being sent, and the like. Having mobile device 202 perform these self-tests frees server 130 to perform other CGM related tasks (e.g., analysis of historical glucose level data collected from a plurality of mobile devices).

FIG. 7 illustrates a flowchart 700 for performing self-tests and determining application compatibility using the results from these self-tests. At 705, mobile device 202 may perform one or more self-tests. As described above, the results from these self-tests can validate whether the CGM application 208 is functioning properly. Mobile device 202 may perform a variety of self-tests including, for example, a screen shot comparison self-test, a notification self-test, a layout self-test, a string self-test, a color comparison self-test, a mobile device state self-test, a self-test of the mobile device's internal components/systems, and the like. Each of these example self-test is described below.

Mobile device 202 may be configured to perform one or more of these self-tests in accordance with a software script loaded onto the mobile device 202. In some implementations, server 130 can provide this script to mobile device 202 by pushing it to the mobile device 202 when a new operating system update is released. In some implementations, server 130 may provide this script on a periodic basis or upon detecting the presence of another application on mobile device 202 that interferes with the operation of the CGM application 208. In some implementations, mobile device 202 can send a request for the script to server 130 when CGM application 208 is updated. This script may specify when the self-test should be performed. For example, the script may cause mobile device 202 to perform one or more self-tests upon detection of a trigger event. As described above with respect to process 410 in FIG. 4, a trigger event may occur, for example, when CGM application 208 is launched on mobile device 202, when the CGM application 208 is upgraded or updated, while the CGM application 208 is being used, while the CGM application 208 is idling in the background of the mobile device, when the operating system on the mobile device 202 has been upgraded or updated, when the mobile device 202 is turned on, upon receiving a request from server 130 or an operator of the mobile device 202, and the like. The script may also specify the parameters to be tested, any test pages or graphical user interface views used during the self-tests, one or more threshold values associated with the self-tests, how to generate or calculate a score based on each self-test's results, and the like. In some implementations, this script may be modified to account for different mobile device characteristics.

In a screen shot comparison self-test, mobile device 202 may compare a model screenshot (i.e., an expected image) with a test screenshot (i.e., an actual image) to determine whether the test screenshot is properly displayed. FIG. 8 illustrates a graphical user interface view 800 for conducting this self-test. The left panel 801 and center panel 802 illustrate an expected image and an actual image, respectively. The right panel 803 illustrates the graphical differences between the expected and actual images. If any objects are present in the "Difference" panel, then the actual image may not be properly generated. In the example of graphical user interface view 800, an exclamation point appears in the "Difference" panel, which indicates that the actual image may be different than the expected image. This difference may be detected in accordance with known methods. Upon completion of this test, the mobile device 202 may generate a result representative of the outcome of this test. This result may be, for example, a Boolean value representative of a difference between the expected and actual images, a numerical score, and the like.

In some implementations, in a notification self-test, mobile device 202 may send a notification to itself and display the received notification. In doing so, mobile device 202 may verify whether the displayed notification appears properly. A notification appears properly if, for example, it is actually triggered, received and/or displayed in its entirety. Upon completion of this test, the mobile device 202 may generate output representative of the test results, such as a numerical score.

In some implementations, mobile device 202 may also conduct a layout test. A layout may specify the position of various objects on a view of a graphical user interface. For example, a title bar may be centered along the top of a graphical user interface view. In performing this test, mobile device 202 may confirm that each object is placed in its correct position on the graphical user interface view. Mobile device 202 may also determine whether any portion of these objects is displayed off-screen. For example, if the title at the top of a graphical user interface view is cut off, then mobile device 202 may determine that graphical user interface view differs from an expected layout and, consequently, is not properly displayed. Upon completion of this test, mobile device 202 may generate a result representative of the outcome of this test. This result may be, for example, a Boolean value representative of whether the layout is incorrectly displayed, a numerical score, and the like.

In some implementations, mobile device 202 may also conduct a test to verify that strings, such as character strings, are properly displayed on graphical user interface views. In doing so, mobile device 202 may determine whether any strings are missing from a graphical user interface view or incorrectly displayed. FIG. 9 illustrates a graphical user interface view 900 for performing a string self-test. Upon completion of this test, the mobile device 202 may generate a result, such as a Boolean value or a numerical score representative of an outcome of the self-test.

In some implementations, mobile device 202 may also conduct a color comparison self-test that tests whether the mobile device 202 is displaying the correct colors. Upon completion of this test, the mobile device 202 may generate a result, such as a Boolean value or a numerical score representative of an outcome of the self-test.

In some implementations, mobile device 202 may also perform a self-test to validate that its own internal components or systems are functioning properly with CGM application 208. For example, in order to validate that the mobile device's communication system is functioning properly, CGM application 208 may send one or more test messages to sensor assembly 101, e.g., using the mobile device's Bluetooth communication system. Upon receiving this test message, sensor assembly 101 may be configured to send an acknowledgment message back to mobile device 202. If mobile device 202 receives this acknowledgment message within a predetermined period of time, then the mobile device's Bluetooth communication system may be functioning properly. In another example, the mobile device 202 may determine whether it has sufficient memory and processing (e.g., CPU) resources to operate CGM application 208. In order to do so, CGM application 208 may be configured to generate a test image, for example. An inability to generate this test image may be indicative of a lack of memory or processing resources to support CGM application 208.

Returning to FIG. 7, mobile device 202 may compile the results from the self-tests at 710 and send them to server 130 at 715. In some implementations, mobile device 202 may send these results one-by-one as mobile device 202 performs each self-test. In some implementations, mobile device 202 may collectively send these test results in one large batch in order to reduce the amount of network traffic. The test results sent at 715 may include, for example, a description of the test, an output of the test (e.g., a Boolean value or a numerical score representative of the results), when the test was conducted, and the like.

At 720, server 130 may determine application compatibility based on the received test results. Generally, the results from each self-test may be evaluated independently of each other. If the failure of a particular test results in a safety risk to the patient, then the CGM application 208 can be shut down. In these implementations, server 130 may have a predetermined list of various self-tests. If server 130 receives a result indicating that any of these self-tests have failed, then server 130 can send a message to mobile device 202 to shut down the CGM application 208. For example, mobile device 202 may perform a self-test to determine if it is properly generating audible alerts. The inability to generate an audible alert can affect the safety of a patient. This situation may occur if, for example, the CGM application 208 determines that the patient's glucose level is low and is unable to generate an audible alert indicating the same. Based on this test result, server 130 may instruct mobile device 202 to shut down the CGM application 208. In some implementations, server 130 may determine application compatibility based on a composite score. This composite score may be calculated in accordance with Equation 1:

$$\text{Composite Score} = \Sigma_i W_i T_i \quad \text{(Equation 1)}$$

In Equation 1, $W_i$ may represent a weight associated with a self-test's numerical score $T_i$. This sum may be calculated over all self-tests i. Using weights may be useful if the results from one self-test are more important than another. The relative importance of each self-test may be adjusted by changing its weight. These weights may be predetermined and provided to server 130 or dynamically changed by the server. While Equation 1 is presented as one possible method for calculating the composite score, other methods can be used including, for example, calculating an average (or weighted average) of all self-test scores, taking the statistical mode of all test scores, and the like.

Server 130 may compare the composite score with one or more numerical ranges. Each range may be associated with a particular level of application compatibility. Table 1, for example, identifies several exemplary numerical ranges:

TABLE 1

Relationship Between Composite Scores and Levels of Compatibility.

| Composite Score | Level of Compatibility |
|---|---|
| 0-100 | Incompatible |
| 101-200 | Partially compatible |
| >201 | Fully compatible |

Server 130 may determine the level of compatibility based on the calculated composite score. If, for example, server 130 calculates a composite score of 50, then the server may determine that the mobile device's CGM application 208 and operating system are incompatible.

Although application compatibility may be assessed based on a numerical score (e.g., a weighted score, an average score, a weighted average score, a statistical mode, and the like), it may also be assessed in other ways. For example, one or more self-tests may be required for application compatibility. As such, pass or failure of these required self-tests may dictate whether an incompatibility is found. These required self-tests may be predetermined by an administrator and saved to the software script used to conduct the self-tests. For example, if the screenshot comparison self-test and the layout self-test are required for application compatibility, then failure of either test may result in an incompatibility. A failure may occur if, for example, the numerical score resulting from a self-test falls below a predetermined threshold value.

Returning to FIG. 7, if server 130 determines that the mobile device's CGM application 208 and operating system are fully compatible, then server 130 may transmit a message at 725 indicating the same to mobile device 202. For example, message 725 may be similar to message 445 and may cause CGM application 208 to operate in a normal manner according to its expected use. As described above, all of the example CGM application modules may be available during normal operation.

If server 130 determines that the mobile device's CGM application 208 and operating system are incompatible, then server 130 may transmit a message at 730 indicating the same to mobile device 202. For example, message 730 may be similar to message 455 and may cause CGM application 208 to disable one or more of its core functions as described above with respect to FIG. 4. Disabling a core function may cause CGM application 208 to become non-operational. In some implementations, CGM application 208 may also display graphical user interface view 600 to indicate that one or more core modules have been disabled and to prompt the user to download any available updates.

If server 130 determines that the mobile device's CGM application 208 and operating system are partially compatible, then server 130 may transmit a message at 735 indicating the same to mobile device 202. For example, message 735 may be similar to message 465 and may cause CGM application 208 to operate in a safe mode by disabling one or more ancillary functions as described above with respect to FIG. 4. In some implementations, CGM application 208 may also display graphical user interface view 620 to indicate that one or more ancillary modules have been disabled and to prompt the user to download any available updates.

EXAMPLES

The following examples are illustrative of several embodiments and implementations in accordance with the present technology. Other example embodiments and implementations of the present technology may be presented prior to the following listed examples, or after the following listed examples.

In some embodiments in accordance with the present technology (example 1), a method includes receiving, by at least one processor, one or more data values from a user equipment having a glucose monitoring application installed on the user equipment, the one or more data values characterizing a version of the glucose monitoring application, a version of an operating system installed on the user equipment, and one or more attributes of the user equipment; determining, by the at least one processor, whether the glucose monitoring application is compatible with the operating system by at least comparing the received one or more data values to one or more test values in a configuration file, the one or more test values including one or more of a range of compatible operating system versions, a wildcard entry of compatible operating system versions, and a regular expression of compatible user equipment attributes; and sending, by the at least one processor, a message to the user equipment based on the determining, the message causing the glucose monitoring application to operate in one or more of a normal mode, a safe mode, and a non-operational mode.

Example 2 includes the method of example 1, in which the one or more data values are received from the user equipment when the glucose monitoring application is launched, when the glucose monitoring application is updated, when the glucose monitoring application is being used, or when the glucose monitoring application is idling.

Example 3 includes the method of example 1, in which the one or more data values are received from the user equipment when the operating system is updated.

Example 4 includes the method of example 1, in which the one or more data values are received from the user equipment when the user equipment is turned on or when the user equipment receives a request from a server communicatively coupled with the user equipment.

Example 5 includes the method of example 1, in which the one or more attributes of the user equipment comprise a manufacturer of the user equipment and a model of the user equipment.

Example 6 includes the method of example 1, in which the message causes the user equipment to display a user interface view on the user equipment while the glucose monitoring application is in the safe mode, the user interface view indicating that one or more ancillary functions are disabled.

Example 7 includes the method of example 6, in which the one or more ancillary functions comprise entering events associated with food consumption.

Example 8 includes the method of example 6, in which the user interface view further indicates that an update for the glucose monitoring application is available.

Example 9 includes the method of example 1, in which the message causes the user equipment to display a user interface view on the user equipment while the glucose monitoring application is in the non-operational mode, the user interface view indicating that one or more core functions are disabled.

Example 10 includes the method of example 9, in which the one or more core functions comprise one or more of generating an alert, displaying a glucose level, and prompting calibration of a glucose sensor assembly.

Example 11 includes the method of example 1, further including sending, by at least one processor, the message a predetermined quantity of times while the glucose monitoring application is operating in the safe mode or the non-operational mode.

Example 12 includes the method of example 1, in which the one or more data values further includes identification information of a transmitter unit of a glucose sensor assembly wearable by a patient user, in which the identification information of the transmitter unit includes one or both of a transmitter device version number and a software version number, and in which the identification information of the transmitter unit is provided to the user equipment in an advertisement packet transmitted from the transmitter to the user equipment; and the method further including determining, by the at least one processor, whether the transmitter unit is compatible with the user equipment by at least comparing the received one or more data values to the one or more test values in the configuration file.

In some embodiments in accordance with the present technology (example 13), a method includes receiving, by at least one processor, one or more data values from a user equipment having a glucose monitoring application installed on the user equipment, the one or more data values representing results from one or more self-tests performed on the user equipment, the one or more self-tests validating one or more features of one or more of the glucose monitoring application and the user equipment; determining, by the at least one processor, whether the glucose monitoring application is compatible with the operating environment based at least on a comparison of the one or more data values with a predetermined list of self-tests; and sending, by the at least one processor, a message to the user equipment based on the determining, the message causing the glucose monitoring application to operate in one or more of a normal mode, a safe mode, and a non-operational mode.

Example 14 includes the method of example 13, in which the determining further comprises generating a composite score based on the one or more data values, in which the composite score is a weighted sum of the one or more data values, an average of the one or more data values, a weighted average of the one or more data values, or a statistical mode of the one or more data values.

Example 15 includes the method of example 13, in which the one or more self-tests comprise one or more of a screenshot comparison self-test, a notification self-test, a layout self-test, a string self-test, a color comparison self-test, a user equipment state self-test, and a self-test of one or more systems of the user equipment.

Example 16 includes the method of example 13, in which the one or more self-tests are performed on the user equipment when the glucose monitoring application is launched, when the glucose monitoring application is updated, when the glucose monitoring application is being used, or when the glucose monitoring application is idling.

Example 17 includes the method of example 13, in which the operating environment includes one or more of an operating system installed on the user equipment and an application which impacts operation of the glucose monitoring application.

Example 18 includes the method of example 17, in which the one or more self-tests are performed on the user equipment when the operating system is updated.

Example 19 includes the method of example 13, in which the one or more self-tests are performed on the user equipment when the user equipment is turned on or when the user equipment receives a request from a server communicatively coupled with the user equipment.

Example 20 includes the method of example 13, further including: providing, by at least one processor, a script to the user equipment, the script causing the user equipment to perform the one or more self-tests.

Example 21 includes the method of example 13, in which the one or more data values are individually received after each of the one or more self-tests are performed or collectively received in a batch after all of the one or more self-tests are performed on the user equipment.

Example 22 includes the method of example 13, in which the message causes the user equipment to display a user interface view on the user equipment while the glucose monitoring application is in the safe mode, the user interface view indicating that one or more ancillary functions are disabled.

Example 23 includes the method of example 13, in which the message causes the user equipment to display a user interface view on the user equipment while the glucose monitoring application is in the non-operational mode, the user interface view indicating that one or more core functions are disabled.

Example 24 includes the method of example 13, in which the glucose monitoring application is associated with a wearable glucose sensor assembly including a transmitter unit that wirelessly communicates with the user equipment, and in which the one or more self-tests further includes a validation of the transmitter unit compatible with the user equipment based on validating identification information of the transmitter unit including one or both of a transmitter device version number and a software version number with configuration information of the user equipment and the glucose monitoring application; the method further including: determining, by the at least one processor, whether the transmitter unit is compatible with the user equipment based at least on a comparison of the one or more data values with the predetermined list of self-tests.

In some embodiments in accordance with the present technology (example 25), a system includes at least one processor; and at least one memory including code which when executed by the at least one processor causes operations of the system including receiving, by the at least one processor, one or more data values from a user equipment having a glucose monitoring application installed on the user equipment, the one or more data values characterizing a version of the glucose monitoring application, a version of an operating system installed on the user equipment, and one or more attributes of the user equipment, determining, by the at least one processor, whether the glucose monitoring application is compatible with the operating system by at least comparing the received one or more data values to one or more test values in a configuration file, the one or more test values including one or more of a range of compatible operating system versions, a wildcard entry of compatible operating system versions, and a regular expression of compatible user equipment attributes, and sending, by the at least one processor, a message to the user equipment based on the determining, the message causing the glucose monitoring application to operate in one or more of a normal mode, a safe mode, and a non-operational mode.

Example 26 includes the system of example 25, in which the one or more data values are received from the user equipment when the glucose monitoring application is launched, when the glucose monitoring application is updated, when the glucose monitoring application is being used, or when the glucose monitoring application is idling.

Example 27 includes the system of example 25, in which the one or more data values are received from the user equipment when the operating system is updated.

Example 28 includes the system of example 25, in which the one or more data values are received from the user equipment when the user equipment is turned on or when the user equipment receives a request from a server communicatively coupled with the user equipment.

Example 29 includes the system of example 25, in which the one or more attributes of the user equipment comprise a manufacturer of the user equipment and a model of the user equipment.

Example 30 includes the system of example 25, in which the message causes the user equipment to display a user interface view on the user equipment while the glucose monitoring application is in the safe mode, the user interface view indicating that one or more ancillary functions are disabled.

Example 31 includes the system of example 30, in which the one or more ancillary functions comprise entering events associated with food consumption.

Example 32 includes the system of example 30, in which the user interface view further indicates that an update for the glucose monitoring application is available.

Example 33 includes the system of example 25, in which the message causes the user equipment to display a user interface view on the user equipment while the glucose monitoring application is in the non-operational mode, the user interface view indicating that one or more core functions are disabled.

Example 34 includes the system of example 33, in which the one or more core functions comprise one or more of generating an alert, displaying a glucose level, and prompting calibration of a glucose sensor assembly.

Example 35 includes the system of example 25, in which the operations further comprise sending, by at least one processor, the message a predetermined quantity of times while the glucose monitoring application is operating in the safe mode or the non-operational mode.

Example 36 includes the system of example 25, in which the one or more data values further includes identification information of a transmitter unit of a glucose sensor assembly wearable by a patient user, in which the identification information of the transmitter unit includes one or both of a transmitter device version number and a software version number, and in which the identification information of the transmitter unit is provided to the user equipment in an advertisement packet transmitted from the transmitter to the user equipment; and in which the operations further include determining, by the at least one processor, whether the transmitter unit is compatible with the user equipment by at least comparing the received one or more data values to the one or more test values in the configuration file.

In some embodiments in accordance with the present technology (example 37), non-transitory computer-readable storage medium including program code which when executed by at least one processor causes operations that include receiving, by the at least one processor, one or more data values from a user equipment having a glucose monitoring application installed on the user equipment, the one or more data values characterizing a version of the glucose monitoring application, a version of an operating system installed on the user equipment, and one or more attributes of the user equipment; determining, by the at least one processor, whether the glucose monitoring application is compatible with the operating system by at least comparing the received one or more data values to one or more test values in a configuration file, the one or more test values including one or more of a range of compatible operating system versions, a wildcard entry of compatible operating system versions, and a regular expression of compatible user equipment attributes; and sending, by the at least one processor, a message to the user equipment based on the determining, the message causing the glucose monitoring application to operate in one or more of a normal mode, a safe mode, and a non-operational mode.

In some embodiments in accordance with the present technology (example 38), a system includes at least one processor; and at least one memory including code which when executed by the at least one processor provides operations including receiving, by the at least one processor, one or more data values from a user equipment having a glucose monitoring application installed on the user equipment, the one or more data values representing results from one or more self-tests performed on the user equipment, the one or more self-tests validating one or more features of one or more of the glucose monitoring application and the user equipment, determining, by the at least one processor, whether the glucose monitoring application is compatible with the operating environment based at least on a comparison of the one or more data values with a predetermined list of self-tests, and sending, by the at least one processor, a message to the user equipment based on the determining, the message causing the glucose monitoring application to operate in one or more of a normal mode, a safe mode, and a non-operational mode.

Example 39 includes the system of example 38, in which the determining further comprises generating a composite score based on the one or more data values, and in which the composite score is a weighted sum of the one or more data values, an average of the one or more data values, a weighted average of the one or more data values, or a statistical mode of the one or more data values.

Example 40 includes the system of example 38, in which the one or more self-tests comprise one or more of a screenshot comparison self-test, a notification self-test, a layout self-test, a string self-test, a color comparison self-test, a user equipment state self-test, and a self-test of one or more systems of the user equipment.

Example 41 includes the system of example 38, in which the one or more self-tests are performed on the user equipment when the glucose monitoring application is launched, when the glucose monitoring application is updated, when the glucose monitoring application is being used, or when the glucose monitoring application is idling.

Example 42 includes the system of example 38, in which the operating environment includes one or more of an operating system installed on the user equipment and an application which impacts operation of the glucose monitoring application.

Example 43 includes the system of example 42, in which the one or more self-tests are performed on the user equipment when the operating system is updated.

Example 44 includes the system of example 38, in which the one or more self-tests are performed on the user equipment when the user equipment is turned on or when the user equipment receives a request from a server communicatively coupled with the user equipment.

Example 45 includes the system of example 38, in which the operations further comprise providing, by at least one processor, a script to the user equipment, the script causing the user equipment to perform the one or more self-tests.

Example 46 includes the system of example 38, in which the one or more data values are individually received after each of the one or more self-tests are performed or collectively received in a batch after all of the one or more self-tests are performed on the user equipment.

Example 47 includes the system of example 38, in which the message causes the user equipment to display a user interface view on the user equipment while the glucose monitoring application is in the safe mode, the user interface view indicating that one or more ancillary functions are disabled.

Example 48 includes the system of example 38, in which the message causes the user equipment to display a user interface view on the user equipment while the glucose monitoring application is in the non-operational mode, the user interface view indicating that one or more core functions are disabled.

Example 49 includes the system of example 38, in which the glucose monitoring application is associated with a wearable glucose sensor assembly including a transmitter unit that wirelessly communicates with the user equipment, and in which the one or more self-tests further includes a validation of the transmitter unit compatible with the user equipment based on validating identification information of the transmitter unit including one or both of a transmitter device version number and a software version number with configuration information of the user equipment and the glucose monitoring application; and in which the operations further comprise determining, by the at least one processor, whether the transmitter unit is compatible with the user equipment based at least on a comparison of the one or more data values with the predetermined list of self-tests.

In some embodiments in accordance with the present technology (example 50), non-transitory computer-readable storage medium including program code which when executed by at least one processor causes operations that include receiving, by the at least one processor, one or more data values from a user equipment having a glucose monitoring application installed on the user equipment, the one or more data values representing results from one or more self-tests performed on the user equipment, the one or more self-tests validating one or more features of one or more of the glucose monitoring application and the user equipment; determining, by the at least one processor, whether the glucose monitoring application is compatible with the operating environment based at least on a comparison of the one or more data values with a predetermined list of self-tests; and sending, by the at least one processor, a message to the user equipment based on the determining, the message causing the glucose monitoring application to operate in one or more of a normal mode, a safe mode, and a non-operational mode.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, audible feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. Other implementations may be within the scope of the following claims.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method comprising:
   receiving, by at least one processor, one or more data values from a user equipment having a glucose monitoring application installed on the user equipment, the one or more data values representing results from one or more self-tests performed on the user equipment, the one or more self-tests validating proper operation of one or more features of one or more of the glucose monitoring application and the user equipment;
   determining, by the at least one processor, whether the glucose monitoring application is compatible with an operating environment based at least on a comparison of the one or more data values with respective values from a predetermined list of results of self-tests; and
   sending, by the at least one processor, a message to the user equipment based on the determining, the message causing the glucose monitoring application to operate in one or more of a normal mode, a safe mode, and a non-operational mode,
   wherein the message causes the user equipment to display a user interface view on the user equipment while the glucose monitoring application is in the safe mode, the user interface view indicating that one or more ancillary functions are disabled; and
   wherein the message causes the user equipment to display a user interface view on the user equipment while the glucose monitoring application is in the non-operational mode, the user interface view indicating that one or more core functions are disabled, wherein the one or more core functions include one or more modules that are essential to the operation of the glucose monitoring application and wherein the one or more ancillary functions include one or more modules that are not essential to the operation of the glucose monitoring application, wherein the core functions includes one or more of generating an alert if a glucose level of a user is outside of a target range, displaying a glucose level, or prompting calibration of a glucose sensor assembly.

2. The method of claim 1, wherein the determining further comprises generating a composite score based on the comparison of the one or more data values.

3. The method of claim 1, wherein the one or more self-tests comprise one or more of a screenshot comparison self-test, a notification self-test, a layout self-test, a string self-test, a color comparison self-test, a user equipment state self-test, and a self-test of one or more systems of the user equipment.

4. The method of claim 1, wherein the one or more self-tests are performed on the user equipment when the glucose monitoring application is launched, when the glucose monitoring application is updated, when the glucose monitoring application is being used, or when the glucose monitoring application is idling.

5. The method of claim 1, wherein the operating environment includes one or more of an operating system installed on the user equipment and an application which impacts operation of the glucose monitoring application.

6. The method of claim 5, wherein the one or more self-tests are performed on the user equipment when the operating system is updated.

7. The method of claim 1, wherein the one or more self-tests are performed on the user equipment when the user equipment is turned on or when the user equipment receives a request from a server communicatively coupled with the user equipment.

8. The method of claim 1, further comprising:
   providing, by at least one processor, a script to the user equipment, the script causing the user equipment to perform the one or more self-tests.

9. The method of claim 1, wherein the one or more data values are individually received after each of the one or more self-tests are performed or collectively received in a batch after all of the one or more self-tests are performed on the user equipment.

10. The method of claim 1, wherein the glucose monitoring application is associated with a wearable glucose sensor assembly including a transmitter unit that wirelessly communicates with the user equipment, and wherein the one or more self-tests further includes a validation of the transmitter unit compatible with the user equipment based on validating identification information of the transmitter unit including one or both of a transmitter device version number and a software version number with configuration information of the user equipment and the glucose monitoring application; the method further comprising:
   determining, by the at least one processor, whether the transmitter unit is compatible with the user equipment based at least on a comparison of the one or more data values with the predetermined list of self-tests.

11. A system comprising:
   at least one processor; and
   at least one memory including code which when executed by the at least one processor provides operations comprising:
      receiving, by the at least one processor, one or more data values from a user equipment having a glucose monitoring application installed on the user equipment, the one or more data values representing results from one or more self-tests performed on the user equipment, the one or more self-tests validating proper operation of one or more features of one or more of the glucose monitoring application and the user equipment,
      determining, by the at least one processor, whether the glucose monitoring application is compatible with an operating environment based at least on a comparison of the one or more data values with respective values from a predetermined list of results of self-tests, and
      sending, by the at least one processor, a message to the user equipment based on the determining, the message causing the glucose monitoring application to operate in one or more of a normal mode, a safe mode, and a non-operational mode, wherein the message causes the user equipment to display a user interface view on the user equipment while the glucose monitoring application is in the safe mode, the user interface view indicating that one or more ancillary functions are disabled; and wherein the message causes the user equipment to display a user interface view on the user equipment while the glucose monitoring application is in the non-operational mode, the user interface view indicating that one or more core functions are disabled, wherein the one or more core functions include one or more modules that are essential to the operation of the glucose monitoring application and wherein the one or more ancillary functions include one or more modules that are not essential to the operation of the glucose monitoring application, wherein the core functions includes one or more of generating an alert if a glucose level of a user is outside of a target range, displaying a glucose level, or prompting calibration of a glucose sensor assembly.

12. The system of claim 11, wherein the determining further comprises generating a composite score based on the comparison of the one or more data values.

13. The system of claim 11, wherein the one or more self-tests comprise one or more of a screenshot comparison self-test, a notification self-test, a layout self-test, a string self-test, a color comparison self-test, a user equipment state self-test, and a self-test of one or more systems of the user equipment.

14. The system of claim 11, wherein the one or more self-tests are performed on the user equipment when the glucose monitoring application is launched, when the glucose monitoring application is updated, when the glucose monitoring application is being used, or when the glucose monitoring application is idling.

15. The system of claim 11, wherein the operating environment includes one or more of an operating system installed on the user equipment and an application which impacts operation of the glucose monitoring application.

16. The system of claim 15, wherein the one or more self-tests are performed on the user equipment when the operating system is updated.

17. The system of claim 11, wherein the one or more self-tests are performed on the user equipment when the user equipment is turned on or when the user equipment receives a request from a server communicatively coupled with the user equipment.

18. The system of claim 11, wherein the operations further comprise providing, by at least one processor, a script to the user equipment, the script causing the user equipment to perform the one or more self-tests.

19. The system of claim 11, wherein the one or more data values are individually received after each of the one or more self-tests are performed or collectively received in a batch after all of the one or more self-tests are performed on the user equipment.

20. The system of claim 11, wherein the glucose monitoring application is associated with a wearable glucose sensor assembly including a transmitter unit that wirelessly communicates with the user equipment, and wherein the one or more self-tests further includes a validation of the transmitter unit compatible with the user equipment based on validating identification information of the transmitter unit including one or both of a transmitter device version number and a software version number with configuration information of the user equipment and the glucose monitoring application; and wherein the operations further comprise determining, by the at least one processor, whether the transmitter unit is compatible with the user equipment based at least on a comparison of the one or more data values with the predetermined list of self-tests.

* * * * *

UNITED STATES PATENT AND TRADEMARK OFFICE
CERTIFICATE OF CORRECTION

PATENT NO. : 10,691,574 B2
APPLICATION NO. : 15/334160
DATED : June 23, 2020
INVENTOR(S) : Issa Sami Salameh et al.

Page 1 of 1

It is certified that error appears in the above-identified patent and that said Letters Patent is hereby corrected as shown below:

In the Specification

In Column 6, Line 31, delete "application-specific" and insert --application specific--.

In Column 6, Line 46, delete "1351)" and insert --135D--.

In Column 7, Line 28, delete "radio-frequency" and insert --radio frequency--.

In Column 7, Line 52, after "receiver" insert --ID,--.

In Column 9, Line 5, delete "computer readable" and insert --computer-readable--.

In Column 9, Line 8, delete "data," and insert --data--.

Signed and Sealed this
Eighth Day of September, 2020

Andrei Iancu
*Director of the United States Patent and Trademark Office*